United States Patent [19]  [11] Patent Number: 4,720,496
Schromm et al.  [45] Date of Patent: Jan. 19, 1988

[54] PYRIDOTRIAZOLOQUINAZOLINES AND TRIAZOLOPYRIDOQUINAZOLINES USEFUL AS ANTIALLERGICS

[75] Inventors: Kurt Schromm, Ingelheim am Rhein; Anton Mentrup, Mainz-Kastel; Ernst-Otto Renth, Ingelheim am Rhein; Armin Fügner, Gau-Algesheim, all of Fed. Rep. of Germany

[73] Assignee: Boehringer Ingelheim KG, Ingelheim am Rhein, Fed. Rep. of Germany

[21] Appl. No.: 870,365

[22] Filed: Jun. 4, 1986

Related U.S. Application Data

[63] Continuation of Ser. No. 565,141, Dec. 23, 1983, abandoned.

[30] Foreign Application Priority Data

Jan. 8, 1983 [DE] Fed. Rep. of Germany ....... 3300477

[51] Int. Cl.$^4$ .................... A61K 31/505; C07D 471/14
[52] U.S. Cl. .................... 514/257; 544/245; 544/247; 544/252; 546/117
[58] Field of Search .................. 544/247, 245; 514/257

[56] References Cited

U.S. PATENT DOCUMENTS 3,847,919 11/1974 Knowles et al. ............... 544/247 X
4,012,387 3/1977 Schwender et al. ............ 544/247 X
4,033,961 7/1977 Schwender et al. ............ 544/247 X
4,083,980 4/1978 Schromm et al. ............... 514/257
4,348,396 9/1982 Kierstead et al. ............... 514/267

FOREIGN PATENT DOCUMENTS 2757929 7/1979 Fed. Rep. of Germany .

Primary Examiner—Donald G. Daus
Assistant Examiner—Diana G. Rivers
Attorney, Agent, or Firm—Weissenberger, Hammond & Littell

[57] ABSTRACT

Compounds of the formula

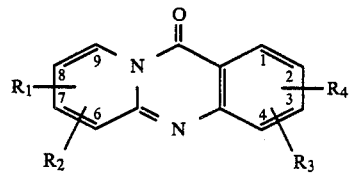

wherein
(a)
 $R_1$ is hydrogen, lower alkyl, lower alkoxy or 8-halo;
 $R_2$ is hydrogen, lower alkyl, lower alkoxy or a fused benzene ring; and
 $R_3$ and $R_4$, together with each other, are —N=N—NH—; or
(b)
 $R_1$ and $R_2$, together with each other, are —N=N—NH—;
 $R_3$ is hydrogen, lower alkyl, lower alkoxy, 2-halo, 3-halo or 4-halo; and
 $R_4$ is hydrogen, lower alkyl, lower alkoxy or a fused benzene ring;

and non-toxic, pharmacologically acceptable salts thereof formed with an inorganic or organic base. The compounds as well as their salts are useful as antiallergics.

8 Claims, No Drawings

PYRIDOTRIAZOLOQUINAZOLINES AND TRIAZOLOPYRIDOQUINAZOLINES USEFUL AS ANTIALLERGICS

This is a continuation of Ser. No. 565,141, filed Dec. 23, 1983, now abandoned.

This invention relates to novel heterocyclic compounds, to methods of preparing them, to pharmaceutical compositions containing them as active ingredients, and to a method of using them as antiallergics.

More particularly, the present invention relates to a novel class of heterocyclic compounds represented by the formula

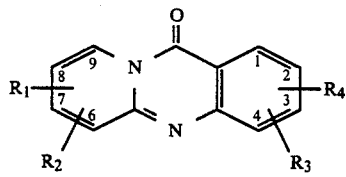
(I)

wherein (a)
$R_1$ is hydrogen, lower alkyl, lower alkoxy or 8-halo;
$R_2$ is hydrogen, lower alkyl, lower alkoxy or a fused benzene ring; and
$R_3$ and $R_4$, together with each other, are —N=N—NH—; or (b)
$R_1$ and $R_2$, together with each other, are —N=N—NH—;
$R_3$ is hydrogen, lower alkyl, lower alkoxy, 2-halo, 3-halo or 4-halo; and
$R_4$ is hydrogen, lower alkyl, lower alkoxy or a fused benzene ring;

and non-toxic, pharmacologically acceptable salts thereof formed with an inorganic or organic base.

In each instance the group —N=N—NH— is connected to two vicinal carbon atoms of the phenyl moiety, so that the following basic structures may exist:

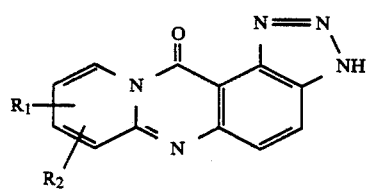
(Ia)

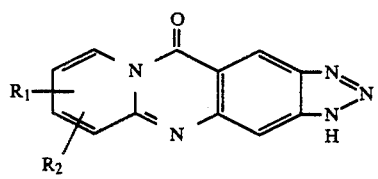
(Ib)

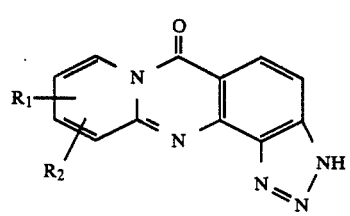
(Ic)

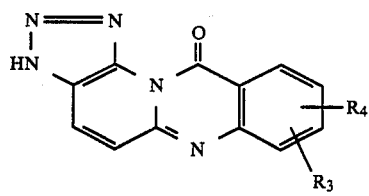
(Id)

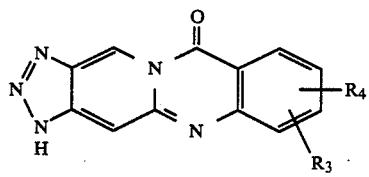
(Ie)

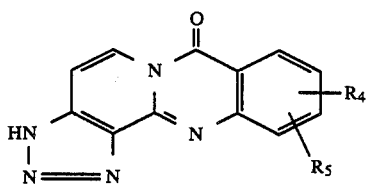
(If)

Correspondingly, in those instances where $R_2$ or $R_4$ is a fused benzene ring, this ring may be fused to the 6/7- or 8/9-position or to the 1/2, 2/3 or 3/4-position, respectively.

The compounds embraced by formula I may be prepared by the following methods:

METHOD A

By reacting a solution of a diamino compound of the formula

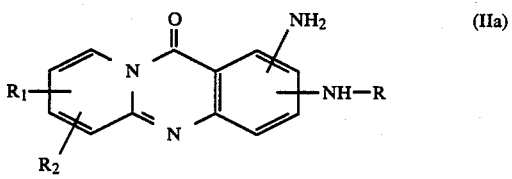
(IIa)

or

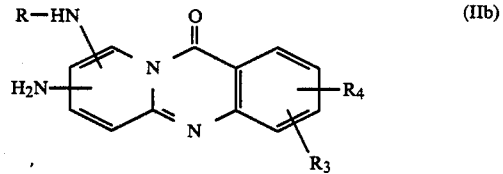
(IIb)

wherein

R is hydrogen or acyl, especially acetyl or another aliphatic acyl of up to 6 carbon atoms; and
$R_1$, $R_2$, $R_3$ and $R_4$ have the meanings previously defined;

and the amino groups are attached to vicinal carbon atoms, for instance in glacial acetic acid or another suitable solvent, with a nitrosing agent such as an aqueous sodium nitrile solution or N-nitroso-diphenylamine at temperatures between about 0° and 100° C. in the presence of an acid. If glacial acetic acid is used as the solvent, it simultaneously takes on the function of the acid. If another solvent is used which itself is not an acid, glacial acetic acid or hydrochloric acid is added to the reaction mixture.

METHOD B

By cyclizing a compound of the formula

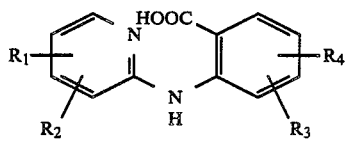
(III)

wherein $R_1$, $R_2$, $R_3$ and $R_4$ have the meanings previously defined, with an acid, especially a mineral acid such as hydrochloric acid.

However, it is not necessary to use a compound of the formula III as such. Instead, it is generally more expedient to start from precursors from which the compounds of the formula III are obtained in situ (these then do not have to be isolated as intermediates).

Thus, an anthranilic acid of the formula

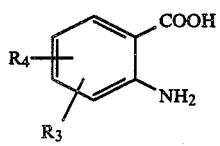
(IV)

or a 2-halopyridine of the formula

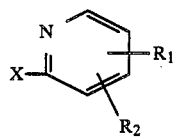
(V)

in which X represents halogen and $R_1$ to $R_4$ have the above meanings, can be converted directly into a compound of the formula I by fusion or heating in a suitable solvent, for example in a dilute alcoholic solution, in the presence of an acid. Fusion is carried out at temperatures between approximately 120° and 200° C., preferably at 160°–175° C. The reaction in solution is advantageously carried out at the boiling point with the addition of an acid.

The starting materials for methods A and B can, if not known, be obtained by conventional methods. Thus, the synthesis of compounds IIa and IIB can be carried out by the following reaction sequences:

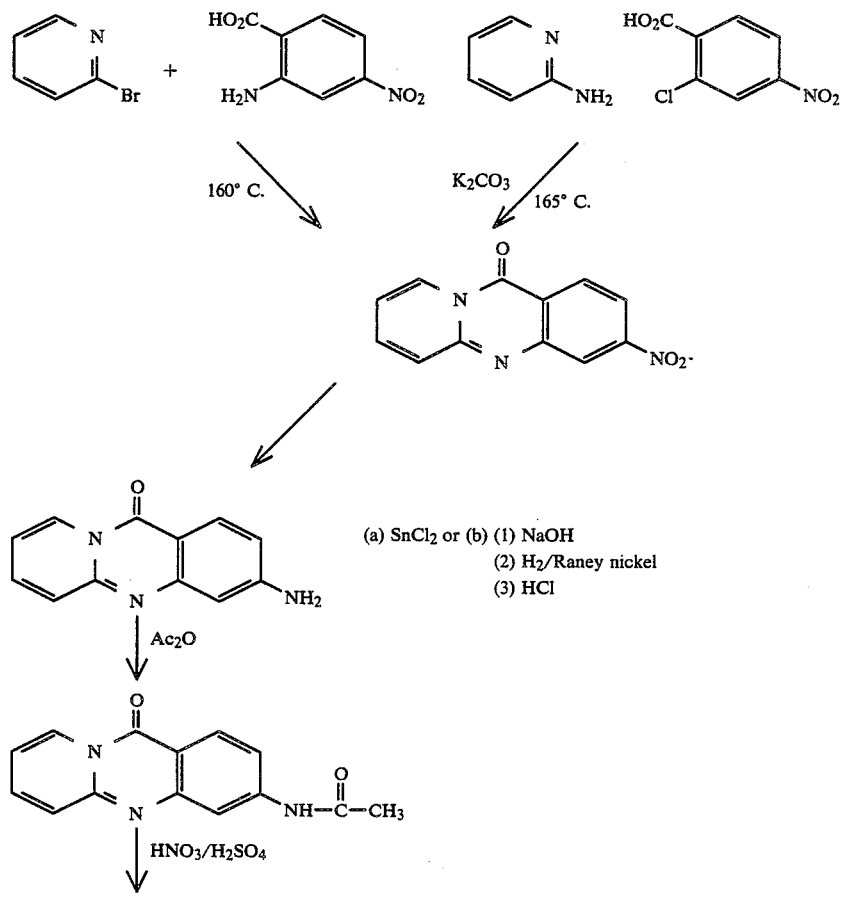

(a) SnCl$_2$ or (b) (1) NaOH
(2) H$_2$/Raney nickel
(3) HCl

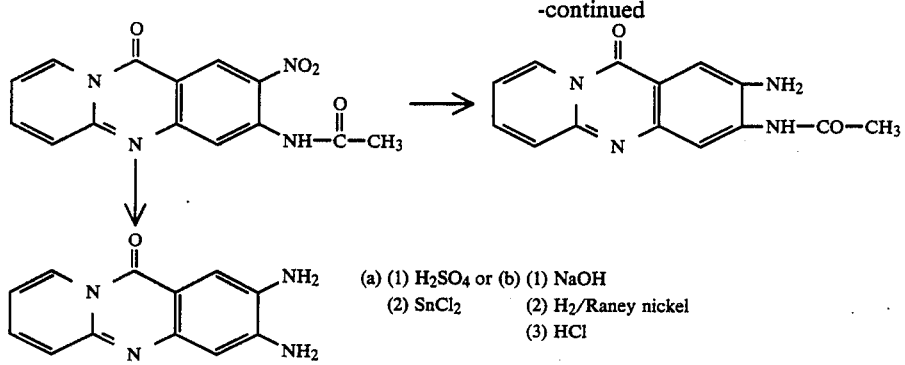

Accordingly, a compound of the formula

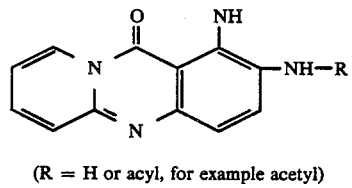

(R = H or acyl, for example acetyl)

can be synthesized from the compound of the formula

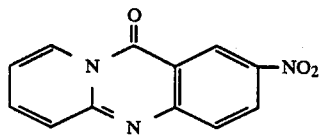

The triazole compounds which serve in method B as precursors for compound III can be synthesized, for example, as follows:

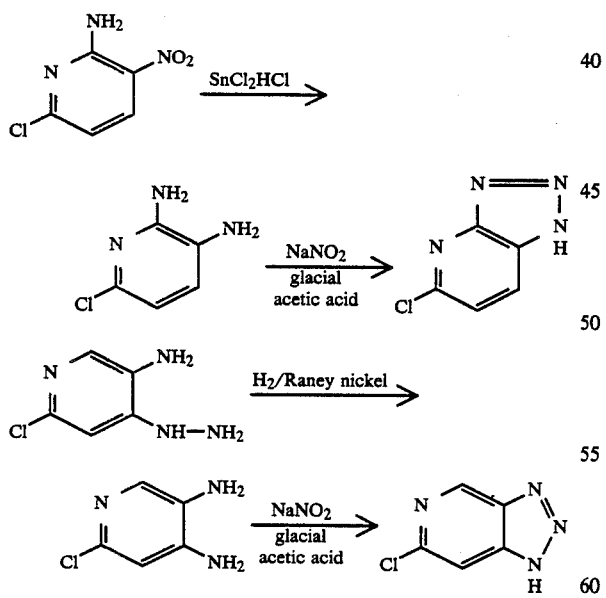

Among the compounds of the formula I, those corresponding to formula Ia, Ib, Id and Ie, especially Ia and Id, are of particular interest. In the pairs of substituents $R_1/R_2$ or $R_3/R_4$, one radical preferably represents hydrogen, while the other represents H, lower alkyl or lower alkoxy. If $R_1$ is a fused benzene ring, this is preferably in 6/7 or 2/3 position in formula I. The lower alkyl and lower alkoxy radicals preferably contain 1 to 4 carbon atoms. Halogen means fluorine, chlorine, bromine or iodine, preferably fluorine or chlorine, especially chlorine. H, methoxy, methyl and isopropyl are to be emphasized, and these radical are preferably in 2- or 8-position, while the group —N=N—NH— is in the 1/2 or 8/9 position in the basic structure.

Only one formula has been given for each of the compounds of the present invention. However, it goes without saying that, because of the triazole grouping, two tautomeric (prototropic) forms exist in each case, for example

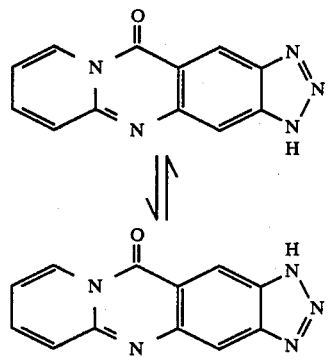

The following examples illustrate the present invention and will enable others skilled in the art to understand it more completely. It should be understood, however, that the invention is not limited solely to the particular examples given below.

EXAMPLE 1

5-Oxo-5H-pyrido[2,1-b]-1H-triazolo[4,5-g]quinazoline

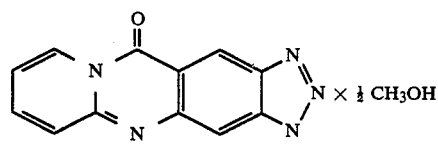

5.98 g of 11-oxo-11H-2,3-diamino-pyrido[2,1-b]quinazoline dihydrochloride, 1.68 g of sodium acetate and 3.96 g of diphenylnitrosamine were heated at 75°–85° C. for one hour in 100 ml of glacial acetic acid. The mixture was then cooled to 20° C., and the precipitate was extracted and washed thoroughly with water. The crude yield of 4 g was converted into the sodium salt by means of 17 ml of 1N sodium hydroxide and purified over a silicagel column with chloroform:methanol=4:1. From the silicagel column, 1.5 g of the title compound were obtained (decomposition point 334°–335° C.), crystallizing with ½ mol of methanol.

| Analysis: C₁₂H₇N₅O × ½CH₃OH | | | |
|---|---|---|---|
| | C % | H % | N % |
| Calculated | 59.29 | 3.56 | 27.67 |
| Found | 59.06 | 4.27 | 27.27 |

EXAMPLE 2

8-Methyl-5-oxo-5H-pyrido[2,1-b]1H-triazolo[4,5-g]quinazoline

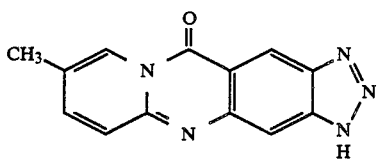

2.8 g of 11-oxo-11H-2,3-diamino-8-methyl-pyrido[2,1-b]-quinazoline dihydrochloride were suspended in 18 ml of water and 7 ml of glacial acetic acid and heated to 40° C. on a water bath. 0.7 g of sodium nitrite were then added, and the mixture was stirred for 60 minutes. The brown crystals were suction-filtered off, washed with water and dried in vacuo at 80° C. The crude product (1.9 g) was purified on a silicagel column with chloroform:methanol: 25% ammonia=5:4:1. The ammonium salt was obtained and converted into the title compound by means of glacial acetic acid.

| Analysis: C₁₃H₉N₅O | | | |
|---|---|---|---|
| | C % | H % | N % |
| Calculated | 62.15 | 3.59 | 27.89 |
| Found | 62.21 | 3.49 | 28.12 |

EXAMPLE 3

4-Oxo-4H-pyrido[2,1-b]1H-triazolo[4,5-f]quinazoline

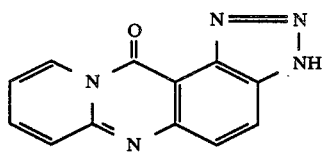

1.7 g of 11-oxo-11H-1-amino-2-acetamido-pyrido[2,1-b]-quinazoline were dissolved in a mixture of 10 ml of glacial acetic acid and 15 ml of water, and heated to 60° C. on a water bath. 1.0 g of sodium nitrite was then added, and the mixture was stirred for 1 hour and worked up as in Example 2. M.p. 380° C. (decomposition).

| Analysis: C₁₂H₇N₅O × ½H₂O | | | |
|---|---|---|---|
| | C % | H % | N % |
| Calculated | 58.54 | 3.25 | 28.46 |
| Found | 58.76 | 3.25 | 28.57 |

The following compound was obtained analogously:

EXAMPLE 3a

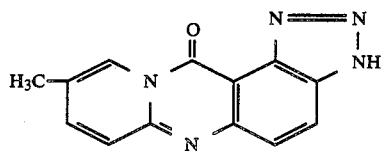

M.p. above 350° C. (decomposition).

| Analysis: C₁₃H₉N₅O | | | |
|---|---|---|---|
| | C % | H % | N % |
| Calculated | 62.15 | 3.59 | 27.89 |
| Found | 62.28 | 3.59 | 27.29 |

The following compounds were also obtained in analogy to the preceding examples:

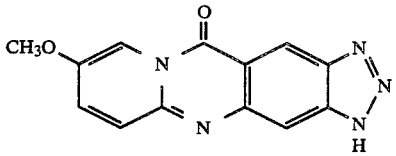

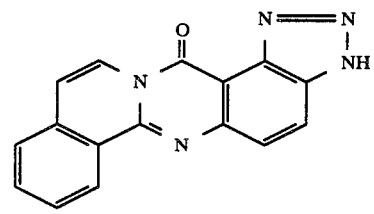

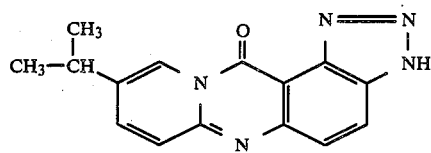

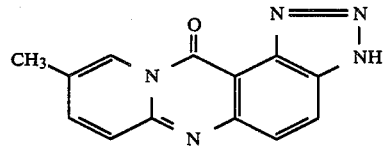

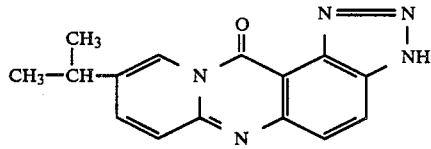

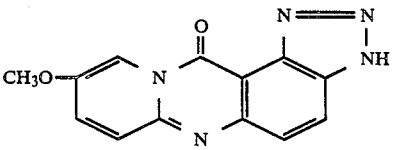

EXAMPLE 4

5-Oxo-5H-triazolo[5,4-e]pyrido[2,1-b]quinazoline

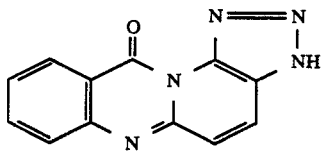

5.74 g of 5-chloro-1H-triazolo[4,5-b]pyridine and 5.48 g of anthranilic acid were refluxed in 120 ml of ethanol and 12 ml of 32% hydrochloric acid for 50 hours. The precipitated crystals of the hydrochloride were suction-filtered off and converted into the title compound by means of sodium acetate. 2 g of the desired compound, crystallized with 1 mol of crystal water, were obtained. Decomposition point: 320° C.

| Analysis: $C_{12}H_7N_5O \times 1H_2O$ | | | |
|---|---|---|---|
| | C % | H % | N % |
| Calculated | 56.47 | 3.53 | 27.45 |
| Found | 59.14/59.48 | 3.53/3.35 | 27.98 |

The following compounds were obtained in analogous manner:

(a) 7-Isopropyl-5-oxo-5H-triazolo[5,4-e]pyrido[2,1-b]quinazoline; decomposition point: 281°–286° C.

| Analysis: $C_{15}H_{13}N_5O$ | | | |
|---|---|---|---|
| | C % | H % | N % |
| Calculated | 64.52 | 4.66 | 25.09 |
| Found | 64.15 | 4.66 | 25.20 |

(b) 7-Methyl-5-oxo-5H-triazolo[5,4-e]pyrido[2,1-b]quinazoline hydrochloride; decomposition point: 355° C.

| Analysis: $C_{13}H_9N_5O \times HCl$ | | | | |
|---|---|---|---|---|
| | C % | H % | N % | Cl % |
| Calculated | 54.26 | 3.48 | 24.35 | 12.35 |
| Found | 53.74 | 3.38 | 24.11 | 12.33 |

(c)

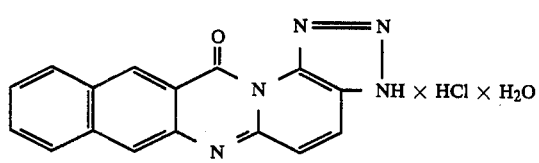

M.p. 380° C. (decomposition).

| Analysis: $C_{16}H_9N_5O \times HCl \times H_2O$ | | | | |
|---|---|---|---|---|
| | C % | H % | N % | Cl % |
| Calculated | 56.22 | 3.51 | 20.50 | 10.50 |
| Found | 56.51 | 3.27 | 19.90 | 10.16 |

(d)

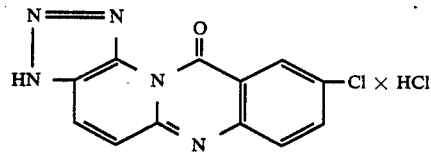

M.p. 380° C. (decomposition).

| Analysis: $C_{12}H_6ClN_5O \times HCl$ | | | | |
|---|---|---|---|---|
| | C % | H % | N % | Cl % |
| Calculated | 46.75 | 2.27 | 22.73 | 23.05 |
| Found | 47.19 | 2.32 | 22.66 | 21.11 |

(e)

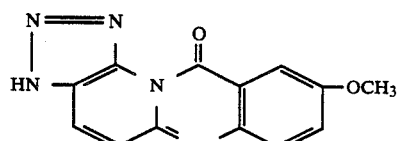

M.p. °C. (decomposition).

| Analysis: $C_{13}H_9N_5O_2$ | | | |
|---|---|---|---|
| | C % | H % | N % |
| Calculated | 58.43 | 3.37 | 26.22 |
| Found | 58.28 | 3.27 | 26.48 |

(f)

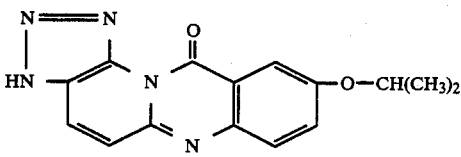

M.p. °C. (decomposition).

| Analysis: $C_{15}H_{13}N_5O \times HCl$ | | | | |
|---|---|---|---|---|
| | C % | H % | N % | Cl % |
| Calculated | 54.30 | 4.22 | 21.12 | 9.65 |
| Found | 54.90 | 4.31 | 21.53 | 9.76 |

The compounds of the present invention, that is, those embraced by formula I above and non-toxic, pharmacologically acceptable salts thereof formed with a basic substance, have useful pharmacodynamic properties. More particularly, they exhibit antiallergic activity in warm-blooded animals such as rats.

As shown by the test pf passive cuntaneous anaphyloxy (PCA test) in the rat, the compounds, in contrast to the commercial product cromoglycinic acid, are also orally active and have a long period of activity. The $ED_{50}$ (oral) in the rat was determined, for example, at 0.29 mg/kg for the compound according to Example 4 and at 0.25 mg/kg for the compound according to Example 4a.

The compounds of the formula I are therefore useful pharmaceuticals. They are of special value in the prevention and treatment of allergic diseases, such as asthma or even hay fever, conjunctivitis, urticaria, eczemas, atopic dermatitis. They also have a muscle-relaxing (broncho-dilating) and vasodilating effect.

The prophylactic or therapeutic dose per kilogram depends on the particular compound, the nature and gravity of the allergic condition and the route of administration. In view of the remarks made above, the individual dose is 0.25-50 mg pulmonally and 5-200 mg orally. Nasally and ocularly, the compounds according to the invention are used in an aqueous buffer solution with 0.5 to 5% active substance.

The pharmaceutical preparations suitable for the various routes of application contain, in addition to a compound of the formula I, conventional excipients and/or carriers and optionally further pharmaceuticals. Among others, combinations with $\beta_2$-adrenergics, xanthines or anticholinergics are possible.

Capsules, tablets, solutions or suspensions are suitable for oral administration.

For pulmonary administration, preferably dry powders with a particle diameter of 0.5-7 μm are introduced into the bronchial region by means of propellent gases or by using powder inhalers.

Lotions, creams, ointments, emulsions and sprays are used for topical application.

The following examples illustrate a few pharmaceutical compositions comprising a compound of the present invention as an active ingredient and represent the best modes contemplated of using the invention. The parts are parts by weight unless otherwise specified.

EXAMPLE 5

Tablets

The tablet composition is compounded from the following ingredients:

| | |
|---|---|
| 5-Oxo-5H—pyrido[2,1-b]-1H—triazolo-[4,5-g]quinazoline | 0.10 part |
| Stearic acid | 0.01 part |
| Glucose | 0.89 part |
| Total | 1.00 part |

Preparation:

The ingredients are compounded in conventional manner, and the composition is compressed into 1 gm-tablets, each of which contains 100 mg of the active ingredient.

EXAMPLE 6

Inhalation aerosol

The aerosol is compounded from the following ingredients:

| | |
|---|---|
| 8-Methyl-5-oxo-5H—pyrido-[2,1-b] 1H—triazolo[4,5-g]-quinazoline | 1.00 parts |
| Soybean lecithin | 0.20 parts |
| Liquefied propellent gas mixture (freon 11, 12 and 14) | q.s. ad 100.00 parts |

Preparation:

The ingredients are compounded in conventional manner, and the composition is filled into aerosol containers equipped with a metering valve which discharges 5 mg of the active ingredient with each actuation.

Any one of the other compounds embraced by formula I or a non-toxic, pharmacologically acceptable salt thereof may be substituted for the particular active ingredient in Examples 5 and 6. Likewise, the amount of active ingredient in these illustrative examples may be varied to achieve the dosage range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

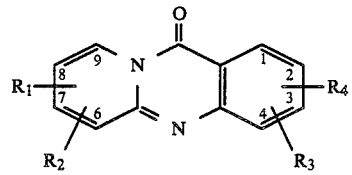

wherein
(a)
  $R_1$ is hydrogen, lower alkyl, lower alkoxy or 8-halo;
  $R_2$ is hydrogen, lower alkyl, lower alkoxy or a fused benzene ring; and
  $R_3$ and $R_4$, together with each other, are —N=N—NH—; or
(b)
  $R_1$ and $R_2$, together with each other, are —N=N—NH—;
  $R_3$ is hydrogen, lower alkyl, lower alkoxy, 2-halo, 3-halo or 4-halo; and
  $R_4$ is hydrogen, lower alkyl, lower alkoxy or a fused benzene ring;
and non-toxic, pharmacologically acceptable salts thereof formed with an inorganic or organic base.

2. The compound of claim 1 which is 5-oxo-5H-pyrido[2,1-b]-1H-triazolo[4,5-g]quinazoline.

3. The compound of claim 1 which is 8-methyl-5-oxo-5H-pyrido[2,1-b]-1H-triazolo[4,5-g]quinazoline.

4. The compound of claim 1 which is 4-oxo-4H-pyrido[2,1-b]-1H-triazolo[4,5-f]quinazoline.

5. The compound of claim 1 which is 5-oxo-5H-triazolo[5,4-e]pyrido[2,1-b]quinazoline.

6. The compound of claim 1 which is 7-isopropyl-5-oxo-5H-triazolo[5,4-e]pyrido[2,1-b]quinazoline.

7. An antiallergic pharmaceutical composition consisting essentially of an inert pharmaceutical carrier and an effective antiallergic amount of a compound of claim 1.

8. The method of preventing or suppressing allergic reactions in a warm-blooded animal in need thereof, which comprises perorally, parenterally, topically or by inhalation administering to said animal an effective antiallergic amount of a compound of claim 1.

* * * * *